United States Patent [19]

Connor et al.

[11] 4,039,579
[45] Aug. 2, 1977

[54] 2-[1-IMINO-2-(METHYLSULFINYL)E-THYL]PHENOLS AND 3-[1-IMINO-2-(METHYLSULFINYL)E-THYL]-2-NAPHTHALENOLS

[75] Inventors: David T. Connor, Parsippany; Patricia A. Young, Madison; Max von Strandtmann, Rockaway, all of N.J.

[73] Assignee: Warner-Lambert Company, Morris Plains, N.J.

[21] Appl. No.: 748,629

[22] Filed: Dec. 8, 1976

[51] Int. Cl.² ............................................. C07C 119/00
[52] U.S. Cl. ...,............................. 260/566 R; 424/325
[58] Field of Search ................................. 260/566 R

[56] References Cited
U.S. PATENT DOCUMENTS 3,801,644   4/1974   von Strandtmann ............... 260/592

*Primary Examiner*—Gerald A. Schwartz
*Attorney, Agent, or Firm*—Albert H. Graddis; Frank S. Chow

[57] ABSTRACT

The present invention relates to 2-[1-imino-2-(methylsulfinyl)ethyl]phenols and 3-[1-imino-2-(methylsulfinyl)ethyl]-2-naphthalenols having the following structural formulas:

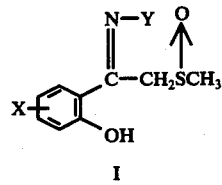 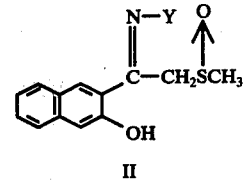

I                                          II wherein X is hydrogen, lower alkyl, halogen, lower alkoxy or hydroxy; Y is hydrogen, lower alkyl or cycloalkyl.

These compounds exhibit antibacterial activity, particularly against gram-positive bacteria, and are useful in the treatment of bacterial infections caused by these organisms.

5 Claims, No Drawings

2-[1-IMINO-2-(METHYLSULFINYL)ETHYL]-PHENOLS AND 3-[1-IMINO-2-(METHYLSULFINYL)ETHYL]-2-NAPHTHALENOLS

The present invention relates to 2-[1-imino-2-(methylsulfinyl)ethyl]phenols and 3-[1-imino-2-(methylsulfinyl)ethyl]-2-naphthalenols which have the following structural formulas:

wherein X is hydrogen, lower alkyl, halogen, lower alkoxy or hydroxy; Y is hydrogen, lower alkyl or cycloalkyl.

In the above definition, lower alkyl and the lower alkyl portions of lower alkoxy are meant to have 1–6 carbon atoms, for example, methyl, ethyl, propyl, isopropyl, butyl, isobutyl and so on.

Cycloalkyl is meant to have 3–8 carbon atoms such as cyclopropyl, cyclobutyl, cyclohexyl and so on.

Halogen is meant to include all four members, i.e., bromine, iodine, fluorine and chlorine.

Also included within the scope of this invention are novel processes for the production of the aforesaid compounds.

The compounds of the present invention exhibit antibacterial activity, particularly against gram-positive cocci such as staphylococcus aureus. Thus, for example, 2-[1-(butylimino)-2-(methylsulfinyl)ethyl]-6-methoxyphenol has the minimal inhibitory concentration of 125 mcg/ml against S. aureus. These compounds are, therefore, useful in the treatment of systemic or topical infections caused by these bacteria.

In order to use the said compounds, they may be formulated with a topically acceptable vehicle such as talc or petrolatum, with the active ingredient being present from about 0.1% to 5%. The topical dosage form is to be applied liberally to the site of the bacterial infection.

To treat systemic infections caused by susceptible organisms they are formulated into dosage forms with inert diluents such as lactose, by technology well-known in the pharmacist's art. The active ingredient in tablets may vary from 25–250 mg. per tablet.

The above compounds I and II are prepared by treating the corresponding ketosulfoxides with ammonia or amines. These reactions may be illustrated by the following scheme:

Generally speaking, the reaction is effected at a low temperature such as −33° C. to about 90° C. depending upon the particular amine selected. For example, with ammonia the reaction is carried out at −33° C. whereas with cyclohexylamine, the reaction is effected at 90° C.

It has been found that the process is quite unexpected. For the process to be successful, the starting ketone must contain an hydroxyl group. Thus 0-hydroxyacetophenone gives 2-(1-iminoethyl)phenol when treated with ammonia, but acetophenone and 2-(methylsulfinyl)-acetophenone give recovered starting material under the same conditions.

The starting o-hydroxyketosulfoxides are prepared as described in U.S. Pat. No. 3,801,644, patented Apr. 2, 1974.

To further illustrate the practice of this invention, the following examples are included:

EXAMPLE 1

2-(1-Iminoethyl)phenol

A solution of 2-hydroxyacetophenone (15 g, 0.11 mole) in liquid ammonia (300 ml) was stirred at −33° for 7 hrs. The ammonia was allowed to evaporate. The residue was recrystallized from ethyl acetate to give yellow crystals (10.1 g, 68%), mp 137°–139°.

Anal. Calcd. for $C_8H_9NO$: C, 71.09; H, 6.71; N, 10.36. Found: C, 71.08; H, 6.74; N, 10.31.

EXAMPLE 2

2-[1-Imino-2-(methylsulfinyl)ethyl]phenol

A solution of 2'-hydroxy-2-(methylsulfinyl)acetophenone (23.5 g, 0.12 mole) in liquid ammonia (450 ml) was stirred at −33° for 9 hrs. The ammonia was allowed to evaporate. The residue was recrystallized from methanol to give yellow crystals (18.5 g, 79%), mp 194°–195°.

Anal. Calcd. for $C_9H_{11}NO_2S$: C, 54.82; H, 5.62; N, 7.10; S, 16.23. Found: C, 54.88; H, 5.69; N, 7.02; S, 16.19.

EXAMPLE 3

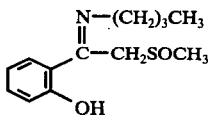

2-[1-(Butylimino)-2-(methylsulfinyl)ethyl]phenol.

A solution of 2'-hydroxy-2-(methylsulfinyl)acetophenone (15 g, 0.076 mole) in n-butylamine (75 ml) was stirred at room temperature for 16 hrs. The reaction mixture was poured into petroleum ether (500 ml) and the product, which precipitated, was filtered off. Recrystallization from ethylacetate-cyclohexane gave yellow crystals (18.2 g, 95%), mp 128°–129°.

Anal. Calcd. for $C_{13}H_{19}NO_2S$: C, 61.63; H, 7.56; N, 5.53; S, 12.66. Found: C, 61.61; H, 7.72; N, 5.55; S, 12.90.

EXAMPLE 4

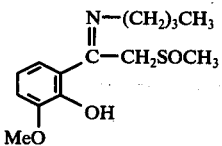

2-[1-(Butylimino)-2-(methylsulfinyl)ethyl]-6-methoxyphenol.

A solution of 2'-hydroxy-3'-methoxy-2-(methylsulfinyl)acetophenone (5 g, 0.022 mole) in n-butylamine (25 ml) was stirred at room temperature for 24 hrs. The reaction mixture was poured into petroleum ether (200 ml) and the product, which precipitated, was filtered off. Recrystallization from ethylacetate gave yellow crystals (6.0 g, 97%), mp 125°–127°.

Anal. Calcd. for $C_{14}H_{21}NO_3S$: C, 59.34; H, 7.47; N, 4.94; S, 11.31. Found: C, 59.35; H, 7.35; N, 4.81; S, 11.42.

EXAMPLE 5

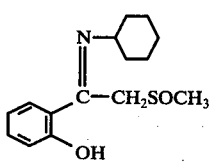

2-[1-(Cyclohexylimino)-2-(methylsulfinyl)ethyl]phenol.

A solution of 2'-hydroxy-2-(methylsulfinyl)acetophenone (15 g, 0.076 mole) in cyclohexylamine (75 ml) was stirred at 90° for 6 hrs. The reaction mixture was cooled and poured into petroleum ether (1 l.). The product was filtered off and washed with hexane to give yellow crystals (20.2 g, 96%), mp 133°–134°.

Anal. Calcd. for $C_{15}H_{21}NO_2S$: C, 64.48; H, 7.58; N, 5.01; S, 11.48. Found: C, 64.74; H, 7.69; N, 5.25; S, 11.49.

EXAMPLE 6

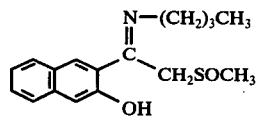

3-[1-(Butylimino)-2-(methylsulfinyl)ethyl]-2-naphthalenol.

A solution of 3'-hydroxy-2-(methylsulfinyl)-2'-acetonaphthone (10 g, 0.040 mole) in n-butylamine (50 ml) was stirred at room temperature for 24 hrs. The reaction mixture was poured into petroleum ether (400 ml) and the product, which precipitated, was filtered off. Recrystallization from absolute ethanol gave light brown crystals (7.0 g, 55%), mp 162°–164°.

Anal. Calcd. for $C_{17}H_{21}NO_2S$: C, 67.29; H, 6.98; N, 4.62; S, 10.57. Found: C, 67.17; H, 7.19; N, 4.62; S, 10.48.

EXAMPLE 7

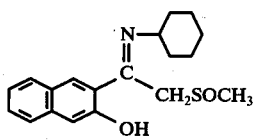

3-[1-(Cyclohexylimino)-2-(methylsulfinyl)ethyl]-2-naphthalenol.

A solution of 3'-hydroxy-2-(methylsulfinyl)-2'-acetonaphthone (10 g, 0.040 mole) in cyclohexylamine (45 ml) was stirred at 90° for 6 hrs. The reaction mixture was cooled and poured into petroleum ether (600 ml). The petroleum ether was decanted from the gummy product, which crystallized from benzene. Recrystallization from ethyl acetate gave brown crystals (2.6 g, 20%), mp 132°–136°.

Anal. Calcd. for $C_{19}H_{22}NO_2S$: C, 69.27; H, 7.04; N, 4.25; S, 9.73. Found: C, 69.16; H, 7.21; N, 4.21; S, 9.99.

We claim:

1. A member selected from the group consisting of compounds of the formula:

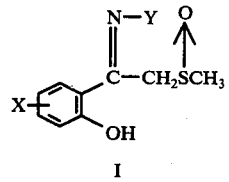

I wherein X is hydrogen, lower alkyl, halogen, lower alkoxy or hydroxy; Y is hydrogen, lower alkyl or cycloalkyl of 3 to 8 carbon atoms.

2. A compound according to claim 1 which is 2-[1-imino-2-(methylsulfinyl)ethyl]phenol.

3. A compound according to claim 1 which is 2-[1-(butylimino)-2-(methylsulfinyl)ethyl]phenol.

4. A compound according to claim 1 which is 2-[1-(butylimino)-2-(methylsulfinyl)ethyl]-6-methoxyphenol.

5. A compound according to claim 1 which is 2-[1-(cyclohexylimino)-2-(methylsulfinyl)ethyl]phenol.

* * * * *